United States Patent
Klabunde et al.

(10) Patent No.: US 7,853,457 B2
(45) Date of Patent: Dec. 14, 2010

(54) AUTOMATIC IDENTIFICATION FOR SPOT MEASUREMENTS

(75) Inventors: Karin Klabunde, Aachen (DE); Heribert Baldus, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 75 days.

(21) Appl. No.: 11/914,950

(22) PCT Filed: May 1, 2006

(86) PCT No.: PCT/IB2006/051356

§ 371 (c)(1), (2), (4) Date: Nov. 20, 2007

(87) PCT Pub. No.: WO2006/126107

PCT Pub. Date: Nov. 30, 2006

(65) Prior Publication Data

US 2008/0162185 A1    Jul. 3, 2008

Related U.S. Application Data

(60) Provisional application No. 60/683,871, filed on May 24, 2005.

(51) Int. Cl.
- G06Q 10/00 (2006.01)
- G06F 19/00 (2006.01)
- A61B 5/00 (2006.01)

(52) U.S. Cl. .............. 705/2; 705/3; 600/300

(58) Field of Classification Search ........... 705/2–4; 600/300; 345/156

See application file for complete search history.

(56) References Cited

U.S. PATENT DOCUMENTS

| | | |
|---|---|---|
| 4,850,009 A | 7/1989 | Zook et al. |
| 4,857,716 A | 8/1989 | Gombrich et al. |
| 5,914,701 A * | 6/1999 | Gersheneld et al. ......... 345/156 |

(Continued)

FOREIGN PATENT DOCUMENTS

| | | |
|---|---|---|
| EP | 0770349 A1 | 5/1997 |
| GB | 2346217 A | 8/2000 |
| WO | 9316636 A1 | 9/1993 |
| WO | 0241237 A1 | 5/2002 |
| WO | 2005006970 A1 | 1/2005 |
| WO | 2005009231 A1 | 2/2005 |

OTHER PUBLICATIONS

Zimmerman, T. G.; Personal Area Networks (PAN): Near-Field Intra-Body Communication; 1995; Masters Dissertation for Massachusetts Institute of Technology; 81 pages.

*Primary Examiner*—Gerald J. O'Connor
*Assistant Examiner*—Joseph D. Burgess

(57) ABSTRACT

A patient monitoring system (8) monitors physiological functions of a plurality of patients (12). Each clinician (10) and each patient (12) has an associated identification device (20, 22), which each includes an identification code corresponding to respective clinician and patient. Each identification device (20, 22) includes a respective body-coupled communication device (24, 26) for communicating the identification code to a medical device (14). The clinician (10) activates the medical device (14) which includes a body-coupled communication device (40) including an ID reader (42). The ID reader (42) scans the area to detect whether the clinician identification is present. After the clinician's identification code is read, the medical device (14) is ready to take measurements. The clinician (10) takes the medical device (14) to the patient (12). The ID reader (42) scans the area to detect the patient identification code. The result of the measurement along with the patient identification code is stored in a medical device memory (56) and later transferred to a patient record in a hospital database (70).

16 Claims, 3 Drawing Sheets

U.S. PATENT DOCUMENTS

| | | |
|---|---|---|
| 6,171,264 B1 | 1/2001 | Bader |
| 6,190,326 B1 | 2/2001 | McKinnon et al. |
| 6,287,252 B1 | 9/2001 | Lugo |
| 6,478,748 B1 | 11/2002 | Kuhn et al. |
| 6,671,563 B1 | 12/2003 | Engelson |
| 2002/0013518 A1 | 1/2002 | West et al. |
| 2002/0060247 A1 | 5/2002 | Krishnaswamy et al. |
| 2002/0188470 A1 | 12/2002 | Hogan |
| 2004/0059599 A1 | 3/2004 | McIvor |
| 2004/0100361 A1 | 5/2004 | Brackett et al. |
| 2005/0101844 A1* | 5/2005 | Duckert et al. .............. 600/300 |
| 2006/0155589 A1* | 7/2006 | Lane et al. .................... 705/4 |

* cited by examiner

AUTOMATIC IDENTIFICATION FOR SPOT MEASUREMENTS

CROSS REFERENCE TO RELATED APPLICATIONS

This application claims the benefit of U.S. provisional application Ser. No. 60/683,871 filed May 24, 2005, which is incorporated herein by reference.

The following relates to medical monitoring arts. It finds particular application in relation to spot measurements in hospitals and will be described with particular reference thereto. However, it is to be appreciated that the invention will also find application in conjunction with patient monitoring in retirement communities, assisted living, at home, and the like.

In health care facilities, especially in the hospitals, clinicians take vital sign spot measurements of a large number of patients, typically, several times a day during regular rounds of a ward. For example, the clinicians may take patient's temperature, blood pressure, and the like. Typically, the clinician comes to the patient, attaches or links the measurement device or sensor and starts the measurement. The result of the measurement is manually recorded in a paper based record. In due course, the result of each manual measurement is manually entered into the corresponding patient record of the hospital information system. Typically, the recordation is done by medical professionals upon returning, for example, to the nurse station, e.g. the result is entered into the patient's record which is selected manually via computer keyboard or other means. The double manual recordation of spot measurements is time-consuming and raises the risk of the human error.

Another problem arises in conjunction with the patient identification. In current hospital solutions, usually an extra action is required to select the correct patient. Typically, the clinician manually selects the paper record of the correct patient, and later on selects correct electronic record when transferring measurement results into the database. In systems with the mobile data collection including a PDA or Laptop, the clinician selects correct patient from the electronic list on PDA/Laptop or scans barcode/RFID tag worn by patient with extra reader. Such procedures are time-consuming and might result in assigning measurement results to wrong patients.

The following contemplates improved apparatuses and methods that overcome the aforementioned limitations and others.

According to one aspect, a patient monitoring system for monitoring physiological functions of each of a plurality of patients is disclosed. A plurality of identification devices, each associated with one of a patient or a clinician, includes an electronic identification code memory for storing an identification code corresponding to one of the patient or the clinician, and body-coupled communication device for communicating the identification code. A medical device includes medical device body-coupled communication device for reading respective communicated identification codes and automatically associating the medical device with the identification codes. A sensor measures a physiological function of each of a plurality of patients. A memory stores results of the measurements and the identification codes.

According to another aspect, a method for monitoring a plurality of patients is disclosed. Wireless identification devices are assigned to one of a patient or a clinician. Each identification device is encoded with an electronic identification code that uniquely identifies one of the patient or clinician. The wireless identification devices automatically associate to a medical device which is linked to the patients. A physiological function of each of the patients is spot measured. The measurements and the identification codes are stored in a measurement memory.

One advantage resides in automatic and unambiguous association of the measurements with the patient and the clinician.

Another advantage resides in automatic transfer of the measurement data into the patient record.

Another advantage resides in use control of the measurement devices.

Another advantage resides in reduced recordation errors.

Numerous additional advantages and benefits will become apparent to those of ordinary skill in the art upon reading the following detailed description of the preferred embodiments.

The invention may take form in various components and arrangements of components, and in various process operations and arrangements of process operations. The drawings are only for the purpose of illustrating preferred embodiments and are not to be construed as limiting the invention.

FIG. 1 diagrammatically shows a medical environment employing an automatic identification system for spot measurement devices;

Figure 1:
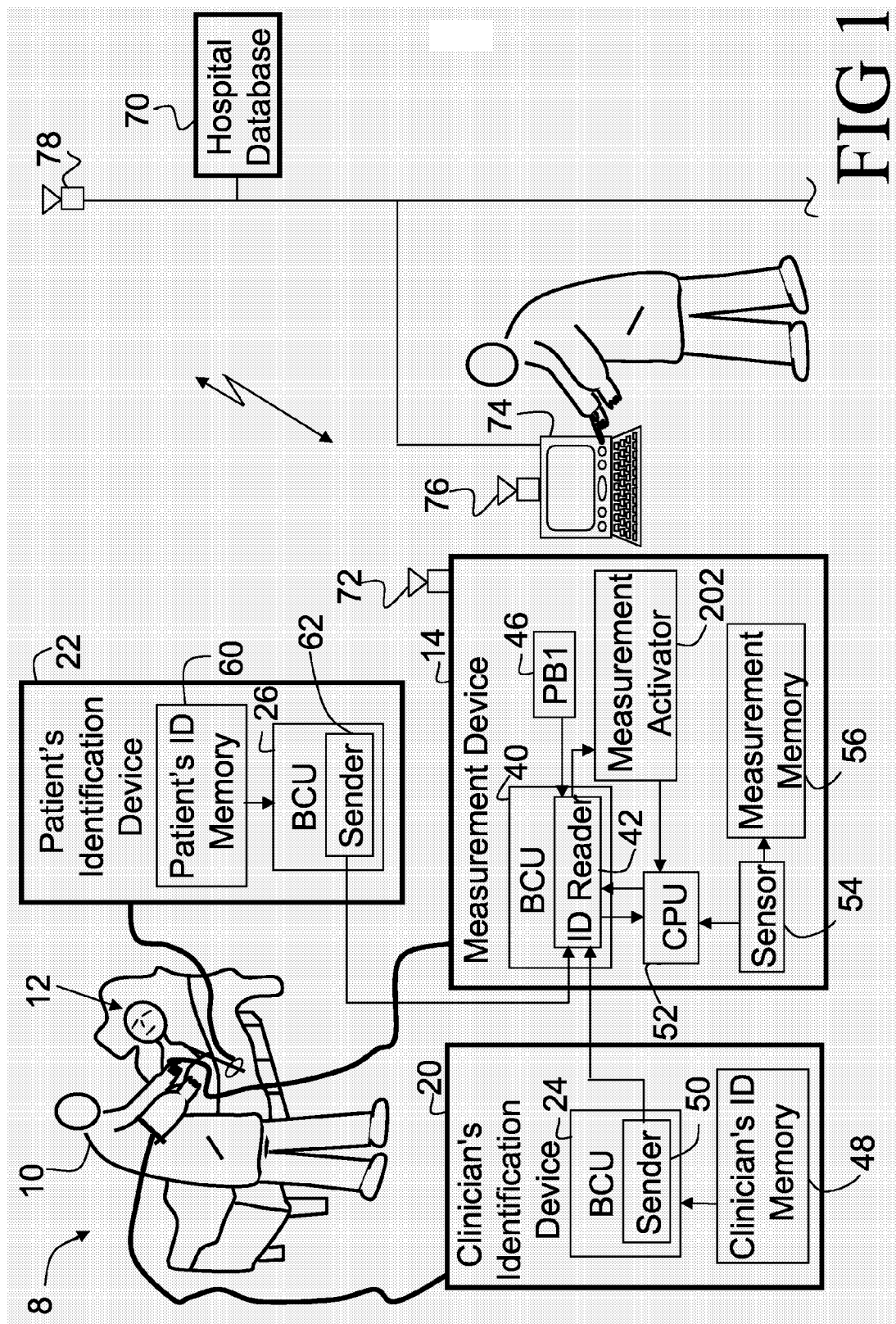

With reference to FIG. 1, in a patient monitoring system 8, an authorized medical person or clinician 10 takes spot measurements, such as temperature, blood pressure and the like, from one or more patients 12 using a measurement unit or medical device 14 which includes a medical probe. The clinician 10 and each patient 12 wear respective clinician's and patient's active identification devices 20, 22 which communicate via body-coupled communication (BCC) with the measurement unit. The clinician's identification device 20 includes at least a unique clinician's identifier (ID) while the patient's identification device 22 includes at least a unique patient's identifier (ID). Such unique identifiers allow relating the measurement results to the specific patient and clinician. Of course, it is also contemplated that more information can be stored in the patient's identification device, for example, name, anamnesis, diagnosis, therapy and the like.

Each identification device 20, 22 is attached to the respective clinician 10 and patient 12 or clinician's and patient's bodies as, wrist or leg bands, badges, implants or the like. Alternatively, the identification device 20, 22 is a non-contact device and is attached in a close proximity, e.g. about 10 cm or so, of the clinician's or the patient's body. Such identification devices do not need skin contact and can be worn in the shirt pocket.

Each identification device 20, 22 includes a respective body-coupled communication unit or BCU 24, 26. The body-coupled communication unit 24, 26 utilizes a near-field body-communication technology, which is based on capacitive coupling and well known in the art, to transmit the patient's or the clinician's ID. Other communications technologies which have properties similar to the body-communication technology can also be used. The medical measurement unit 14 includes a communication unit 40 including an integrated ID reader 42 to request and read the transmitted patient's and/or clinician's ID, via BCC communication. The ID reader 42 is an intelligent device which is capable of distinguishing between the clinician's ID and the patient's ID. Typically, the clinician 10 activates the medical measurement device 14 by an activating means such as a switch, a pushbutton or PB1 46, or other devices commonly used to turn electrical devices on and off. It is also contemplated that the ID reader 42 can be activated when the clinician 10 takes the medical measurement unit 14 in his hand or touches the measurement unit 14. The activating means 46 triggers the ID reader 42 which starts looking for active identification devices such as the clinician's identification device 20. The clinician's ID is withdrawn from a clinician's ID memory 48 and transmitted to the medical device 14 by a sender 50 which is integrated with the clinician's BCU 24. If the ID reader 42 receives and reads the clinician's ID, it completes the activation of the measurement device 14, which is now ready to take measurements of one or more vital parameters, e.g. SPO2, temperature, blood pressure. The clinician 10 starts a round of the ward and takes the measurement unit 14 to one or more patients.

The measurement unit 14 includes a processing unit or CPU 52, a sensor 54, and a measurement memory 56. Upon completion of the measurement unit activation, the ID reader 42 starts looking for an active identification device of the patient 12. When the measurement unit is touching or proximate to a patient, the patient's ID is withdrawn from a patient's ID memory 60 and transmitted to the medical device 14 by a sender 62 which is integrated with the patient's BCU 22. Upon receiving of the patient's ID by the ID reader 42, the measurement unit 14 takes the measurement via the sensor 54 and, in one embodiment, attaches a time stamp to the measurement. Of course, the measurement can be taken and the ID read in either order. The result of the measurement is stored in the measurement memory 56. The record at least includes the patient's ID, the clinician's ID, and the measured value. In one embodiment, the record includes other parameters such as day, time, type of the measurement device used, and other. If required, more measurements for other patients are performed. After finishing the ward round, the clinician 10 returns to a data input area, such as a nurse station, and transfers the data to a patient record in a hospital database 70. For a transmission of the measurement data from the measurement unit to the hospital database, the measurements unit includes an auxiliary communication interface 72 which can include a wired or wireless communications link by using Bluetooth, ZigBee, WLAN, and the like. E.g., the transfer of the collected data from the medical measurement unit 14 to the hospital database 70 can be done via cable, docking station 74, or wirelessly via transmitting/receiving link 76, 78.

Figure 2:
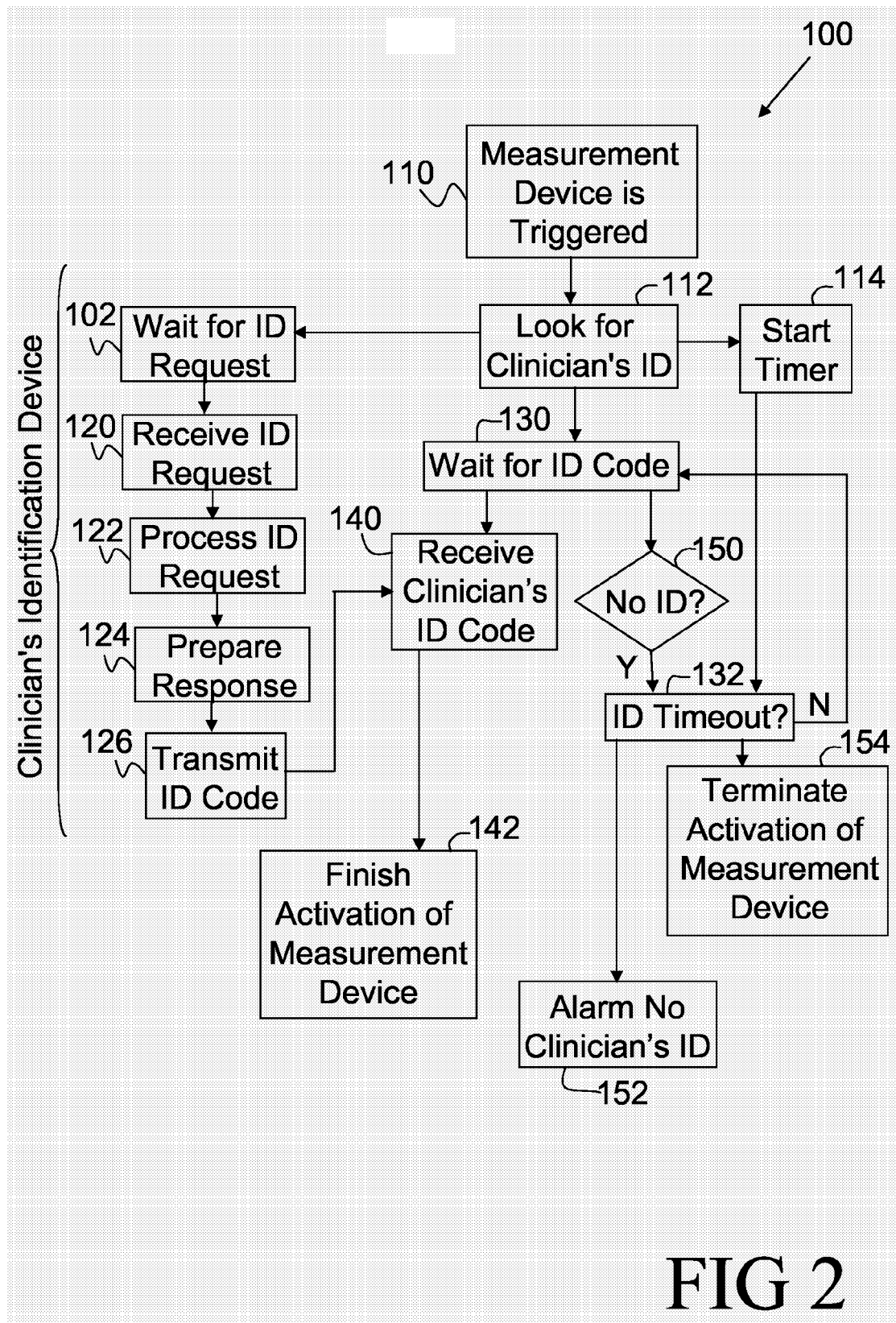
FIG. 2 shows a portion of a process flow of the identification system.

With continuing reference to FIG. 1 and further reference to FIG. 2, a measurement device activation routine 100 is triggered by the clinician 10. Prior to triggering the measurement device activation routine 100, the clinician's identification device 20 is in an idle state and waits 102 for a request to transmit the clinician's ID. The measurement device 14 is triggered 110. The ID reader 42 starts looking 112 for the clinician's ID by pattern designed to distinguish or only detect clinician's ID. At the same time, a timer is started 114. The request for transmission of the clinician's ID code is received 120 by the clinician's BCU 20. The ID request is processed 122 and a response is prepared 124. The clinician's ID is withdrawn from the clinician's ID memory 48 and transmitted 126 to the measurement device 14. The ID reader 42 waits 130 for reception during the prespecified time T, e.g. ID timeout 132 such as 15 sec. In one embodiment, the system is configured to continue requesting the clinician ID several times (if the request was not yet successful). A number of retries is a parameter which is configured in advance for the measurement unit 14. If the clinician's ID code is received 140 within a prespecified time interval T, the activation of the measurement device is finished 142. The measurement device 14 is ready to be taken to the patient 12 for measurements. If no clinician's ID code is received 150 during the T period, an alarm "no clinician ID" is raised 152 and activation of the measurement unit is terminated 154. In this manner, no other person than an authorized clinician can use the system when there is no clinician's ID.

Figure 3:
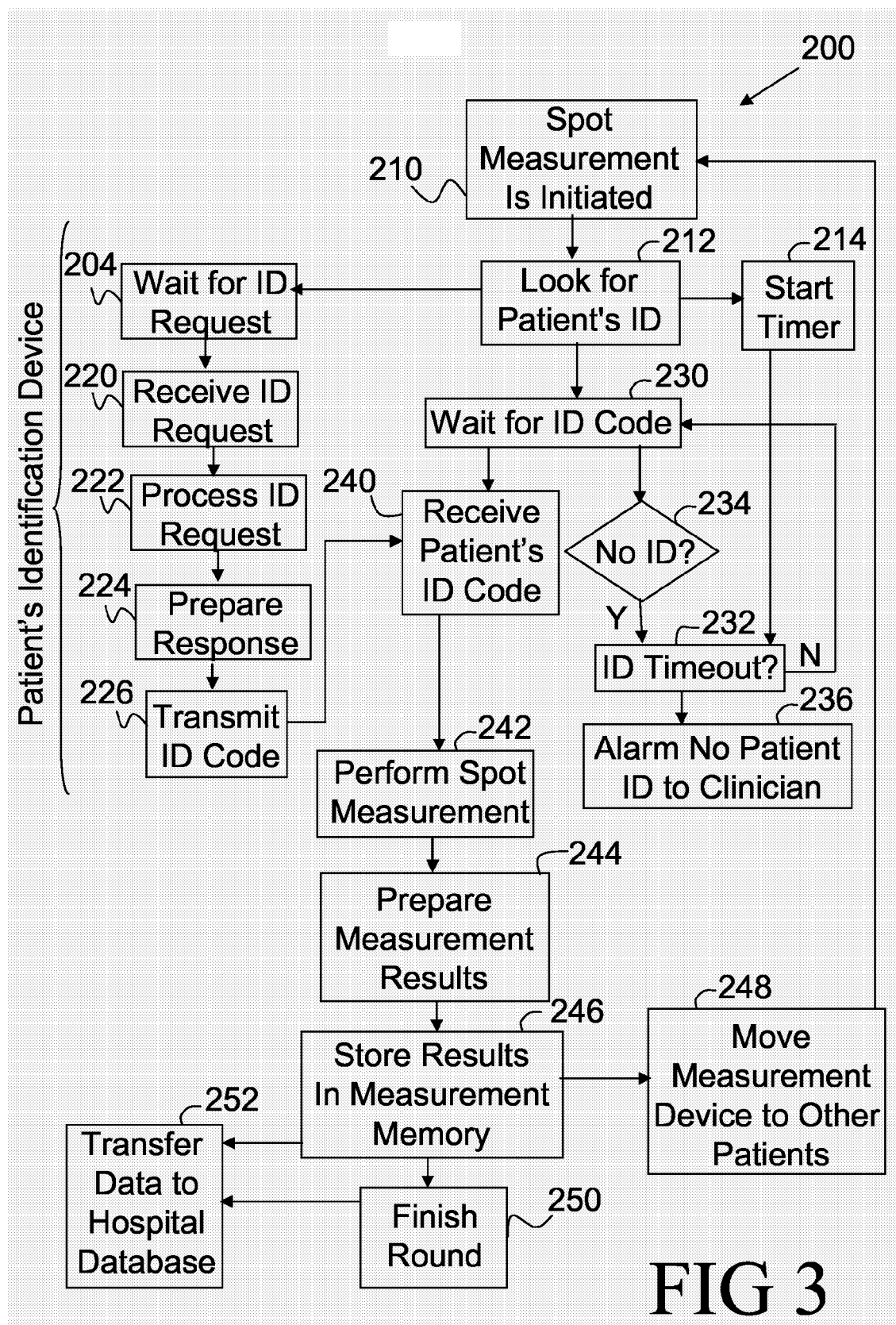
FIG. 3 shows another portion of a process flow of the identification system.

With continuing reference to FIG. 1 and further reference to FIG. 3, a spot measurement routine 200 is initiated by the clinician 10 via a measurement activator 202 such as a second push button. Prior to the initiation of the spot measurement routine 200, the patient's BCU 22 is in an idle state and waits 204 for the request to transmit the patient's ID. The spot measurement is initiated 210. The measurement device 14 starts looking 212 for the patient's ID. At the same time, a timer is started 214. The request for transmission of the patient's ID is received 220 by the patient's BCU 26. The ID request is processed 222 and a response is prepared 224. The patient's ID code is withdrawn from the patient's ID memory 60 and transmitted 226 to the measurement device 14. The ID reader 42 waits 230 for reception during the prespecified time T, e.g. ID timeout 232 such as 15 sec. If no patient's ID code is received 234 during the T period, an alarm "no patient ID" is raised 236. The clinician can take corresponding steps such as retry the patient identification, check whether the patient wears the identification device, manually enter the name of the patient, and take other appropriate steps. If the patient's ID code is received 240 within a prespecified time interval T, the measurements are performed 242. The result of the measurements is prepared 244 and stored 246 in the measurement memory 56. The spot measurement device 14 is moved 248 to other patients. The ID reader 42 reads one patient ID after another in the manner described above, the clinician 10 takes measurements one patient after another, and the measurements of each patient are stored in the measurement memory 56. After the ward round is finished 250, all measurements are transferred 252 to the hospital database 70.

While the clinician 10 makes the ward round from one patient to the next, the measurement unit 14 regularly checks, e.g. with prespecified time interval such as 1 min, whether the clinician is still present to make sure that no unauthorized person uses the measurement device 14. The measurement device performs the check in the manner described above, by requesting and reading the clinician's ID. If no clinician ID is detected, the measurement unit 14 can change into an inactive state.

Instead of a single measurement, a series of measurements for the same patient 12 can be performed. The measurement device 14 is attached to the patient 12 for a longer period of time, e.g. 10 minutes, as may be appropriate to the measurements made. The measurement device 14 is then transferred to the next patient. After all measurements are performed, the measurement data is transferred to the hospital database 70. In one embodiment, the measurements are performed during certain time intervals and stored in the measurement memory 56. The clinician 10 comes at certain time internals with an auxiliary device to read the patient ID and download corresponding measurement data into the auxiliary device. (This transfer could also be done via body-coupled communication.) The measurement data is transferred from the auxiliary device to the hospital database 70.

In one embodiment, the clinician 10 takes patient's measurements with several measurement devices 14 each of which includes a corresponding BCU with an ID reader. The measurement devices 14 cooperate to ensure that a correct ID of the authorized clinician and a correct ID of the patient are read. The measurement devices 14 perform measurements and record the measurement data along with the patient's and the clinician's ID, and optionally the date and time of the measurement, into corresponding measurement memory portion of each measurement device. The clinician 10 comes at certain time internals with an auxiliary device to read each patient's ID and download corresponding measurement data from the measurement devices into the auxiliary device. The measurement data is transferred from the auxiliary device to the hospital database 70, and, optionally, the identifier of the measurement device including its type and serial number or other device specific identification.

Alternatively, a master measurement device is configured to collect the data from the measurement devices. The measurement devices send the measurement data to the master measurement device. In this case, the clinician collects all data from the master measurement device into the auxiliary device.

Optionally, a security mechanism based on secret keys and a challenge-response protocol protects the information sent between the clinician's and patient's identification devices 20, 22 and the ID reader 42.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A patient monitoring system for monitoring physiological functions of each of a plurality of patients, the system comprising:
   a plurality of identification devices, each associated with one of a corresponding one of a plurality of patients including:
      an electronic identification code memory which stores a patient identification code which identifies the corresponding to one of the patients, and
      a patient body-coupled communication device capacitively coupled with the corresponding patient which communicates the identification code via near field communications; and
   a medical device including:
      a sensor which spot measures a physiological function of each of a plurality of patients;
      a medical device body-coupled communication device which capacitively couples with each patient during spot measuring and automatically reads the respective patient identification codes via near field communications and automatically associates physiological function measurements with the patient identification code of the corresponding patient;
      and
      a memory which stores the associated physiological functional measurements and patient identification codes.

2. The system as set forth in claim 1, further including:
   a clinician identification device including:
      an electronic clinician identification code memory which stores a clinician identification code, and
      a clinician body-coupled communication device which capacitively couples to a clinician using the medical device to communicate the clinician identification code to the medical device using the near field communications; and
      wherein the medical device body coupled communication device automatically associates the clinician identification code of the clinician who uses the medical device with the corresponding generated physiological function measurement and patient identification code.

3. The system as set forth in claim 2, wherein the medical device further includes:
   a medical device activator which triggers the clinician body-coupled communication device to transmit the electronic clinician identification code.

4. The system as set forth in claim 2, further including:
   a measurement activator which activates the medical device in response to receiving the electronic clinician identification code using the near field communication and triggers the patient body-coupled communication device to transmit the electronic patient identification code using the near field communications.

5. The system as set forth in claim 4, further including:
   a hospital database which downloads the physiological function measurements along with the respective patient identification code and clinician identification code from the medical device memory.

6. The system as set forth in claim 1, further including:
   a clinician identification device including:
      an electronic clinician identification code memory which stores a clinician identification code, and
      a clinician body-coupled communication device which capacitively couples to the clinician and communicates the clinician identification code via near field communications; and
   wherein the clinician identification device communicates via near-field communications with the medical device when the clinician is capacitively coupled with the medical device and the patient identification device communicates via near-field communications with the medical device when the patient is capacitively coupled with the medical device.

7. The system as set forth in claim 6, further including:
   a hospital database which downloads measurements along with the respective patient and clinician identification codes from the medical device memory.

8. A method for monitoring a plurality of patients, comprising:
   capacitively coupling patient wireless identification devices to each of a plurality of patients, each patient identification device communicating via near field communications and being encoded with an electronic patient identification code that uniquely identifies the patient and communicates the patient identification code via near field body coupled communications;
   capacitively coupling clinician wireless identification devices to each of a plurality of clinicians, each clinician identification device communicating via near field communications and being encoded with an electronic clinician identification code that uniquely identifies the clinician and communicates the clinician identification code via the near field body coupled communications;
   capacitively coupling the clinician with a medical monitoring device and communicating the clinician identification code using a medical device to the medical monitoring device via near field communications;
   capacitively coupling the medical monitoring device with each one of the patients, communicating the patient identification code of each patient to which the medical monitoring device is capacitively coupled via the body coupling communications and spot measuring a physiological function of each patient with the medical device;

automatically communicating the patient identification code of each patient wireless identification device to the medical monitor via the near field communications in conjunction with the spot measuring of each patient and associating each patient identification code with the spot measurement of the corresponding patient;

storing the spot measurements and the patient and clinician identification codes in a measurement memory in the medical monitoring device; and downloading the stored spot measurements and identifications codes to a database.

9. The method as set forth in claim 8, further including:

triggering a transmission of the electronic clinician identification code to the medical monitoring device via the near field communications.

10. The method as set forth in claim 8, further including:

assigning wireless patient identification devices to the selected patients, the electronic patient identification code of each patient identification device being encoded to uniquely identify the selected patient which it is assigned to.

11. The method as set forth in claim 10, further including:

in response to receiving the electronic clinician identification code, activating the medical monitoring device; and triggering a transmission of the electronic patient identification code to the medical monitoring device via the near field communication.

12. The method as set forth in claim 11, further including:

transferring the results of measurements along with the respective clinician and patient identification codes from the medical monitoring device into a hospital database.

13. A patient monitoring system for monitoring physiological functions of each of a plurality of patients, the system comprising:

a clinician identification device including:
an electronic clinician identification code memory which stores the clinician identification code, and
a clinician body-coupled communication device which communicates the clinician identification code of a clinician to whom it is capacitively coupled via near field communications;

a patient identification device including:
an electronic patient identification code memory which stores a patient identification code, and
a patient body-coupled communication device which communicates the patient identification code of a patient with whom it is capacitively coupled via body coupled communications; and a medical device including:
a medical device body-coupled communication device which automatically receives respective communicated identification codes via body coupled communications from a clinician or patient to whom it is capacitively coupled;
a sensor which spot measures a physiological function of each of a plurality of patients;
a memory which stores results of spot measurements measured by the sensor in conjunction with the patient identification code corresponding to each spot measurement and the clinician code of the clinician that used the medical device to make each spot measurement; and
a communication interface which transfers the stored sport measurements, the stored patient identification codes, and the stored clinician identification codes to a hospital database.

14. A spot measurement device for measuring a physiological function of a plurality of patients, the device comprising:

a sensor which measures at least one physiological function of a patient;

a body-coupled communication device which automatically electronically receives a patient identification code from the patient via near field communications contemporaneously with measuring the physiological function of a patient with whom it is capacitively coupled; and a memory which stores data indicative of the measured physiological function associated with the contemporaneously received patient identification code.

15. The device as set forth in claim 14, wherein the body-coupled communication device further retrieves a clinician identification code via near field communication which identifies a clinician capacitively coupled to and operating the measurement device to measure the physiological function.

16. The device as set forth in claim 14, further including:

a timestamp which is attached to the measurement and indicative of at least a time at which an associated measurement is taken;

a medical device identification code which is stored in a medical device identification code memory; and wherein the stored data includes the timestamps associated with each measured physiological function and the medical device identification code withdrawn from the medical device identification code memory.

* * * * *